United States Patent [19]

Freeman

[11] Patent Number: 5,403,742
[45] Date of Patent: Apr. 4, 1995

[54] BIOREACTOR FOR PRODUCTION OF PRODUCTS WITH IMMOBILIZED BIOFILM

[75] Inventor: Amihay Freeman, Ben Shemen, Israel

[73] Assignee: Ramot University Authority Ltd., Tel Aviv, Israel

[21] Appl. No.: 114,275

[22] Filed: Sep. 1, 1993

[51] Int. Cl.$^6$ .................. C12M 1/10; C12M 11/00; C12M 5/00; C12M 1/02

[52] U.S. Cl. ................... 435/312; 435/174; 435/176; 435/177; 435/240.23; 435/310; 435/316; 435/288

[58] Field of Search .......... 435/174, 176, 177, 240.23, 435/310, 312, 316, 288

[56] References Cited

U.S. PATENT DOCUMENTS

| | | | |
|---|---|---|---|
| 3,402,103 | 9/1968 | Amberg et al. | 435/164 |
| 3,925,165 | 12/1975 | Muller | 435/312 X |
| 4,760,028 | 7/1988 | deBrayne et al. | 435/316 |
| 5,266,476 | 11/1993 | Sussman et al. | 435/240.23 |

FOREIGN PATENT DOCUMENTS 2055397 3/1981 United Kingdom .

*Primary Examiner*—David M. Naff
*Attorney, Agent, or Firm*—Mark M. Friedman

[57] ABSTRACT

A bioreactor is provided for production of products by biosynthesis or biotransformation using a biofilm of immobilized cells. The bioreactor includes a horizontal cylindrical housing and a central rotatable shaft which extends along the axis of the housing. Connected to the central shaft are one or more screens which are oriented parallel to the shaft, with a small gap between the shaft and the screen. The bioreactor further includes a slidable blade which is mounted onto the shaft, through a set of poles, and which is located at a fixed distance from the screen so that the blade is made to pass over the screen by the force of gravity as the shaft rotates, as by the action of a rotating external magnet. An example of use of the bioreactor is the production of Y-decalactone from castor oil using *Tyromyces sambuceus*.

9 Claims, 1 Drawing Sheet

BIOREACTOR FOR PRODUCTION OF PRODUCTS WITH IMMOBILIZED BIOFILM

FIELD AND BACKGROUND OF THE INVENTION

The present invention relates to bioreactors and, more particularly, to bioreactors which can be used to support a biofilm of immobilized microorganisms and/or cells which are, or which are capable of producing through biosynthesis or biotransformation, desirable products (hereinafter "biofilm").

In the last few years much effort has been directed toward the development of continuous controlled processes for the production of pharmaceuticals, food additives, enzymes, antibodies and the like, through the use of immobilized microbial plant or mammalian cells. Various cells and microorganisms have been and are being studied in this context. Of primary importance are the filamentous fungi which form the basis of a number of commercially important processes for the production of antibiotics, organic acids and enzymes.

A variety of bioreactotrs for use with immobilized biofilms are known. Examples of these, which relate to filamentous fungi, include the glass ring fixed bed reactor and the rotating biological contactor (RBC) described in Anderson J. G., 1983, in "The Filamentous Fungi", (Smith J., Berry, D. R., Kristiansen, B., eds.) Edward Arnold Pub., London, 4:145-170, and the spouted bed reactor described in Webb, C., Fukuda, H., Atkinson, B., 1986, Biotech. Bioeng., 28:41-50, both of which articles are incorporated by reference as if fully set forth herein. Although each of these systems has certain advantages and strengths, each system leaves something to be desired.

A bioreactor which makes efficient use of immobilized filamentous fungi and similar microorganisms must meet certain criteria. First, the bioreactor must be simple, must operate under sterile conditions and must be readily capable of scale-up to commercial production. Second, the mixing and aeration within the bioreactor must be moderate in order to preserve an active fungus biofilm and avoid shearing, or otherwise injuring, the fungi. Third, provision must be made for the continuous removal of excess fungal biomass while preserving an active culmring seed within the bioreactor. Fourth, the bioreactor must offer mixing which will prevent the phase separation of various immiscible phases. Finally, the bioreactor must accommodate the continuous removal of products during operation under sterile conditions, while at the same time removing any undesirable by-products which, if allowed to accumulate, would interfere with the efficient operation of the process.

There remains a widely recognized need for, and it would be highly advantageous to have, a bioreactor suitable for use with immobilized biofilms, for example, microorganisms such as filamentous fungi, which would have advantages in the above respects, and which will, in addition, afford good contact, low shear and emulsion stabilization.

SUMMARY OF THE INVENTION

According to the present invention, there is provided a bioreactor for production of products using an immobilized biofilm, comprising: (a) a substantially cylindrical housing substantially horizontally oriented, the housing including a feed inlet and a products outlet, the housing further including means for maintaining desired temperatures; (b) a rotatable shaft extending substantially parallel to, and substantially centrally located within, the housing; (c) at least one screen connected to, oriented parallel to, and extending in a direction radially outward from, the shaft, the at least one screen serving to immobilize the biofilm; and (d) a slidable blade mounted onto the shaft and located at a selected distance from the screen so that the blade passes radially over, and substantially parallel to, the screen as the shaft rotates.

According to further features in preferred embodiments of the invention described below, the bioreactor further includes a slidable blade mounted onto the shaft and located at a selected distance from the screen so that the blade passes radially over, and substantially parallel to, the screen as the shaft rotates, the sliding of the blade being over poles which are connected to, and which are oriented radially away from, the rotatable shaft, the sliding being activated by the force of gravity.

According to still further features in the described preferred embodiments, the screen and shaft are separated by a gap.

According to yet further features of preferred embodiments, at least a portion of the rotatable shaft includes a magnet at one of its ends and the rotatable shaft is rotated through the rotation of an external magnet. Alternatively, the rotatable shaft may be directly coupled to an outside motor.

The present invention successfully addresses the shortcomings of the presently known configurations by providing a simple and rugged bioreactor which is easily scaled-up to commercial scale, which can be used to provide an effective support to immobilized biofilms including, but not limited to, filamentous fungi.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
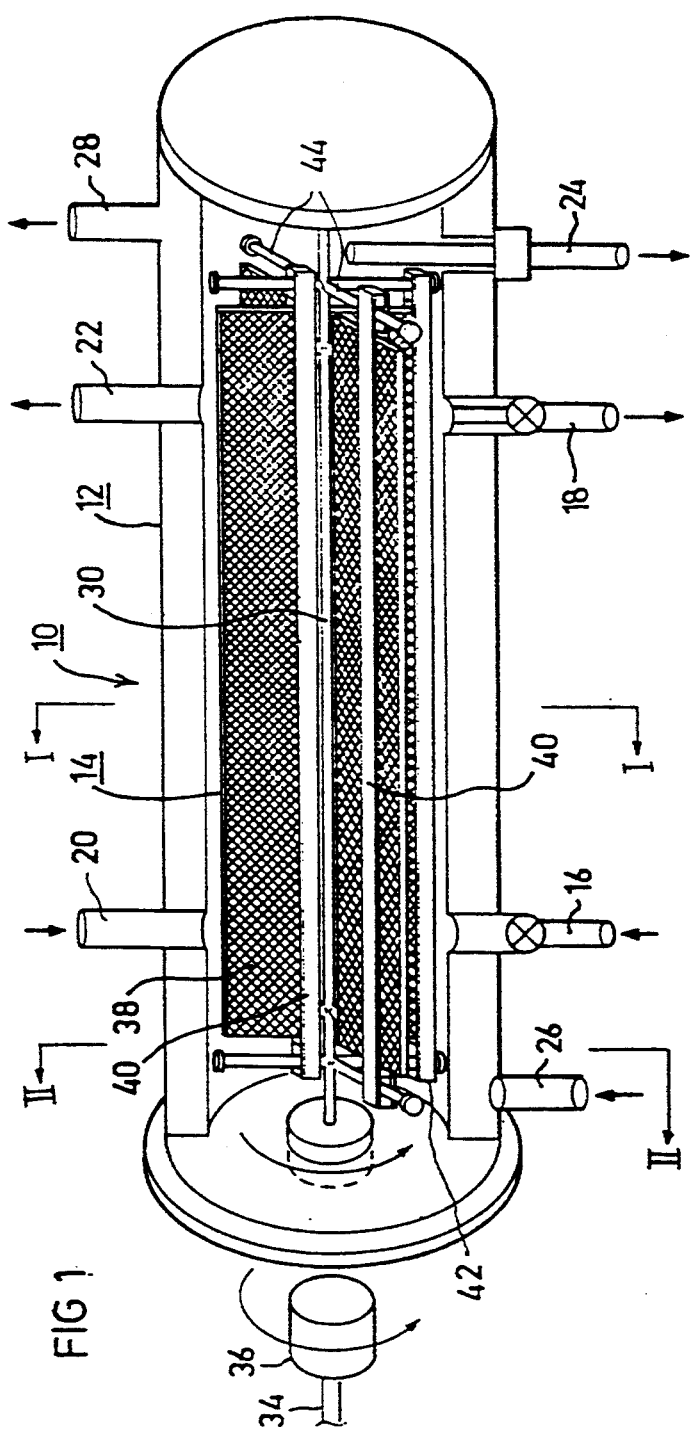
FIG. 1 is a perspective drawing of one embodiment of bioreactor according to the present invention.

The present invention is of a bioreactor which can be used in the continuous biosynthesis or biotransformation of desirable products using immobilized biofilms, for example, microorganisms, such as filamentous fungi.

The principles and operation of a bioreactor according to the present invention may be better understood with reference to the drawing and the accompanying description.

Figure 3:
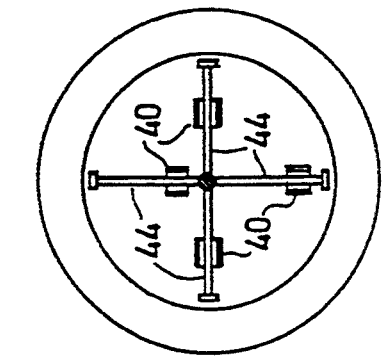
FIG. 3 is a side cross-sectional view of the bioreactor of FIG. 1 along the section line b—b.
Figure 2:
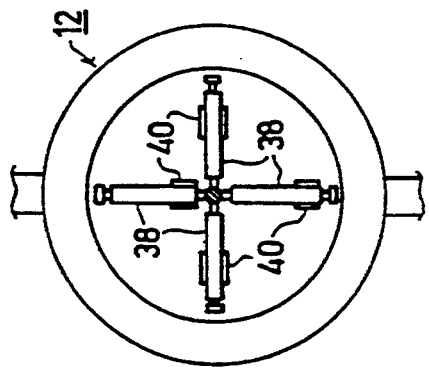
FIG. 2 is a side cross-sectional view of the bioreactor of FIG. 1 along the section line a—a.

Referring now to the drawings, FIGS. 1-3 illustrate key features of a bioreactor according to the present invention. The bioreactor 10 is made up of two basic portions—a housing 12 and the rotating unit 14.

Housing 12 is similar to comparable units which are currently in use in certain applications. Housing 12 is preferably in the shape of a closed cylindrical and can be made from a large variety of materials which are capable of withstanding heat sterilization, including, but not limited to, plastic, metal, glass, ceramic and the like.

The diameter and length of housing 12 are dictated by process conditions and scale.

Housing 12 may include, for example, a medium inlet 16 through which raw materials and, whenever necessary, inoculant cells or microorganisms, are fed to the continuous process taking place in bioreactor 10. Housing 12 further includes a medium outlet 18 through which products and by-products, unreacted raw materials and biomass can leave bioreactor 10.

Housing 12 further includes an air inlet 20 for bringing oxygen to bioreactor 10 and an air outlet 22 for removing the air and carbon dioxide produced by the microorganisms or cells.

To maintain a substantially fixed liquid level in bioreactor 10, housing 12 may further include an overflow outlet 24 which may be in the form of a pipe extending upwards into bioreactor 10 so that the inlet portion of the pipe is at the desired liquid level of bioreactor 10.

To maximize the efficiency of the process, it may be advantageous to control the process temperature. This can be accomplished in a number of ways, one of which involves the use of a water jacket as part of housing 12. Housing 12 thus includes a water jacket inlet 26 and a water jacket outlet 28.

Housing 12 differs from most commonly found bioreactors in that it is oriented substantially horizontally rather than vertically.

Located inside housing 12 is rotating unit 14 which includes a centrally located rotatable shaft 30 extending substantially parallel to the axis of housing 12, i.e., substantially horizontally.

Rotatable shaft 30 may be rotated using any suitable means, including through a direct connection to a motor located outside of bioreactor 10. Preferably, rotatable shaft 30 includes at least one end which is, or which is rigidly connected to, an internal magnet 32. A motor (not shown) rotates a shaft 34 which effects the rotation of an external magnet 36 which, in turn, causes internal magnet 32 and rotatable shaft 30 to rotate. The other end of rotatable shaft 30 may be passively rotatably anchored (not shown) in the opposite end of bioreactor 10. Use of such a rotating system obviates the need to seal shaft 34 at its point of entry into the bioreactor and facilitates the ready sterilization of the bioreactor.

Connected to rotatable shaft 30 in any suitable fashion is one or more screens 38 made of suitable material, such as, for example, stainless steel, polypropylene or cloth, among many possibilities, and having a suitable mesh size selected to optimize a specific application. Screens 38 may have any suitable mesh size and geometry and may, in addition, be modified by the inclusion of various structures, such as a polymer coating or microbeads, onto the screen surfaces. Alternatively, or additionally, some or all of the surfaces of screens 38 may be chemically modified or treated, so as to enhance their effectiveness. The system depicted in FIG. 1 illustrates a system which includes four screens 38, disposed at 90° intervals, but more or fewer screens 38 may also be used. Each screen 38 is oriented parallel to rotatable shaft 30 and extends in a direction radially outward from shaft 30.

Preferably, the connection between rotatable shaft 30 and screen 38 is localized so as to leave a certain gap between rotatable shaft 30 and the inner edge of screen 38 for a substantial portion, preferably nearly all, of the extent of screen 38.

Preferably, rotating unit 14 further includes a slidable blade mechanism 40 which is mounted onto rotatable shaft 30, one blade mechanism 40 per screen 38. Most preferably, blade mechanism 40 includes a pair of parallel blades straddling the corresponding screen 38 and connected to each other through a pair of connectors 42, one at each end of blade mechanism 40. Connectors 42 are slidable over a pair of poles 44 which are connected to, and which extend radially outward from, rotatable shaft 30.

The blades of blade mechanism 40 are situated so as to be at a fixed and pre-determined distance above and below screen 38, the distance being pre-determined to optimize the effectiveness of blade mechanism 40. As rotating unit 14 rotates, the force of gravity causes blade mechanisms 40 to move alternately radially inward and outward along poles 44. In the process, the blades 'shave' the accumulated biomass growing on screens 38 and extending beyond a certain fixed distance above and below screen 38 thereby removing a certain amount of inactive or aging biomass and allowing for additional growth of new and active biofilm.

A bioreactor according to the present invention could be operated as follows. To start the process, a suitable medium containing the desired microorganism or cell inoculant would be fed to the bioreactor under sterile conditions. The screens, whose mesh size is carefully pre-selected to optimize the bioreactor performance, serve to sift and capture the microorganisms or cells from the medium during the mixing process. The captured microorganisms or cells serve as growth sites for the generation of additional biomass on the screens.

Aeration is effected during the portion of travel of the screen in the air in the upper part of the housing. The blades serve to continually reduce the size of the biomass collected on the screens so as to keep it at the desired pre-selected optimum for maximizing growth. The continual shaving of the surface of the biomass serves to renew the surface and maximize product formation. The biomass removed from the screens by the blades exits the bioreactor with the products. The gentle mixing action serves to stabilize, with or without the aid of emulsifiers, any emulsions with might be present.

As an example of one application of a bioreactor according to the present invention which has already been successfully implemented, one can cite the production of Y-decalactone from castor oil, using the filamentous fungus *Tyromyces sambuceus*. The *Tyromyces sambuceus* fungus is highly effective in converting castor oil to Y-decalactone in a reaction sequence which is believed to include the conversion of castor oil to 12-hydroxy-9-octadecenoic acid which is then converted to 10-hydroxy-7-hexadecenoic acid which, in turn, is converted to 4-hydroxydecanoic acid which finally is converted to 4-decalactone, or Y-decalactone.

While the invention has been described with respect to a limited number of embodiments, it will be appreciated that many variations, modifications and other applications of the invention may be made, including the use of a bioreactor according to the present invention with a wide variety of microorganisms or cells in the production of an almost endless list of valuable products.

What is claimed is:

1. A bioreactor for production of products using an immobilized biofilm, comprising:
    (a) a substantially cylindrical housing substantially horizontally oriented, said housing including a feed inlet and a products outlet, said housing further including means for maintaining desired temperatures;

(b) a rotatable shaft extending substantially parallel to, and substantially centrally located within, said housing;

(c) at least one screen connected to, oriented parallel to, and extending in a direction radially outward from, said shaft, said at least one screen serving to immobilize the biofilm; and (d) a slidable blade mounted onto said shaft and located at a selected distance from said screen so that said blade passes radially over, and substantially parallel to, said screen as said shaft rotates.

2. A bioreactor as in claim 1 wherein said blades are slidable over poles which are connected to, and which are oriented radially away from, said rotatable shaft.

3. A bioreactor as in claim 2 wherein said slidable blade is activated by gravity.

4. A bioreactor as in claim 1 wherein said screen and said shaft are separated by a gap.

5. A bioreactor as in claim 1 wherein at least a portion of said rotatable shaft includes a magnet at one of its ends and said rotatable shaft is rotated through the rotation of an external magnet.

6. A bioreactor as in claim 1 wherein said screen is made of stainless steel.

7. A bioreactor as in claim 1 wherein said screen is made of polypropylene.

8. A bioreactor as in claim 1 wherein said housing includes an air inlet and an air outlet.

9. A bioreactor as in claim 1 wherein said means for maintaining desired temperatures includes a water jacket having an inlet and an outlet in said housing.

* * * * *